(12) United States Patent
Lee

(10) Patent No.: US 6,567,161 B1
(45) Date of Patent: May 20, 2003

(54) THREE DIMENSIONAL LEAD INSPECTION SYSTEM

(75) Inventor: Pao Meng Lee, Melaka (MY)

(73) Assignee: ASTI Holdings Limited (SG)

( * ) Notice: Subject to any disclaimer, the term of this patent is extended or adjusted under 35 U.S.C. 154(b) by 0 days.

(21) Appl. No.: 09/723,985

(22) Filed: Nov. 28, 2000

(51) Int. Cl.$^7$ .............................................. G01N 21/00
(52) U.S. Cl. ............................ 356/237.1; 356/237.4; 356/237.5; 250/559.08; 250/559.34
(58) Field of Search .................... 356/237.1, 237.2, 356/237.4, 237.5, 394, 395, 396, 399; 382/8, 145, 146, 150, 151; 250/559.29, 559.31, 559.34, 223 R

(56) References Cited

U.S. PATENT DOCUMENTS

| | | | | |
|---|---|---|---|---|
| 5,249,239 A | * | 9/1993 | Kida | 382/8 |
| 5,311,304 A | * | 5/1994 | Monno | 356/399 |
| 5,909,285 A | * | 6/1999 | Beaty et al. | 356/394 |
| 5,999,640 A | * | 12/1999 | Hatase et al. | 382/151 |
| 6,088,108 A | * | 7/2000 | Toh et al. | 356/237.1 |
| 6,242,756 B1 | * | 6/2001 | Toh et al. | 250/559.34 |
| 6,243,164 B1 | * | 6/2001 | Baldwin et al. | 356/237.1 |
| 6,307,210 B1 | * | 10/2001 | Suzuki et al. | 250/559.08 |

* cited by examiner

Primary Examiner—Frank G. Font
Assistant Examiner—Sang H. Nguyen
(74) Attorney, Agent, or Firm—Christopher J. Rourk; Akin Gump Strauss Hauer & Feld, LLP

(57) ABSTRACT

A semiconductor device lead inspection apparatus and method are provided for capturing images of the semiconductor edges and leads along two optical axes which have different directions in a plane perpendicular to the semiconductor device edge. One image is a direct backlit image of the device. A second image taken along a direction corresponding to a second optical axis is reflected into a direction corresponding to the first optical axis. By forming two images it is possible to locate the leads of the semiconductor device in three dimensions.

22 Claims, 6 Drawing Sheets

THREE DIMENSIONAL LEAD INSPECTION SYSTEM

BACKGROUND OF INVENTION

This invention relates to devices for inspecting the leads of integrated circuit or semiconductor devices. Known semiconductor device lead inspection systems are used to determine the position and orientation of semiconductor device leads after manufacture to find defects in the leads, such as bent leads, twist leads and the like. Prior art systems are mainly intended to provide a two dimensional view of the leads, which cannot be used to measure the lead standoff and coplanarity. In some cases, two or three imaging devices with various viewing angles are used to inspect device leads. In existing devices, the position of lead standoff may be measured from an optical reference point such as a track upon which the semiconductor device is positioned for purposes of inspection. In this event, the accuracy of positioning the device on the inspection station can affect the accuracy of the measurements of the lead positions.

It is an object of the present invention to provide images of a semiconductor device and its leads which provides geometrical information of the lead positions with respect to the edge of the semiconductor device body.

SUMMARY OF THE INVENTION

In accordance with the invention, there is provided an apparatus for providing first and second backlit images of a semiconductor device edge and leads extending therefrom. The images are representative of first and second viewing angles corresponding to first and second different optical axes as measured in a plane perpendicular to the device edge. The apparatus include at least one illuminator which provides diffuse backlit illumination of the device edge and leads in directions corresponding to first and second optical axis. A camera is arranged on an opposite side of the device edge from the illuminator along the first optical axis and oriented to form a direct image on the first optical axis. A reflector is arranged on the opposite side of the device edge and leads, along a second optical axis for deflecting a backlit image of the device edge and leads in a direction corresponding to the first optical axis toward the camera.

In one arrangement, the illuminator is an illuminated platform for holding the device. The camera is preferably arranged on a side of the device opposite the illuminated platform when the device is received on the platform. Where the device includes device edges and leads on two opposite sides of the device, two deflectors can be arranged for deflecting images corresponding to two of the second optical axes. In one embodiment the deflector comprises a prism, which may be a triangular right angle prism with a preferable edge angle of about 30 degrees. In this case, the deflecting can be internal reflection in the prism. The prism may have a surface which is paralleled to the first optical axis and a surface which is substantially perpendicular to the first optical axis. In another arrangement, the deflector may comprise a mirror. The mirror may form a plane which has an angle of 60 degrees from its normal to the first optical axis. In another arrangement there may be provided two illuminators, one for illuminating the device edge and leads along each of the optical axes. In this case, in one arrangement at least one of the illuminators may be arranged to move between an illuminating position and a withdrawn position which facilitates movement of a semiconductor device into an inspection position.

According to the invention, there is provided a method for providing first and second backlit images of a semiconductor device edge and leads extending therefrom. The images represent first and second viewing angles corresponding to first and second different optical axes as measured in a plane perpendicular to the device edge. The device edge and leads are illuminated with backlit light diffuse illumination radiating in directions corresponding to the first and second optical axes. A first backlit image of the device edge and leads is captured along a direction corresponding to the first optical axis. A second backlit image of the device edge and leads is deflected from a direction corresponding to the second optical axis to a direction corresponding to the first optical axis and the second backlit image is captured as deflected.

The illumination can be from one illuminator which is arranged to radiate in directions corresponding to the first and second optical axes toward the device edge and the leads. The first and second backlit images may be captured on a single image plane of a camera on a side of the device opposite the illuminator. In one arrangement, backlit images of device edges and leads on two opposite sides of a semiconductor device can be captured. A first backlit image of the two edges and leads is captured in a direction corresponding to a first optical axis and a second backlit image of each of the device edges and leads is deflected from directions corresponding to two of the second optical axes in directions corresponding to the first optical axis and the two deflected backlit images are captured. The deflecting can be accomplished using a prism or a mirror. The prism may provide internal reflection. The illumination may be provided from a first illuminator in a direction corresponding to the first optical axis and a second illuminator illuminating in directions corresponding to the second optical axis. The first illuminator may be moved between a first position in which it illuminates the device edge and a second withdrawn position which facilitates movement of a semiconductor device into an inspection station.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
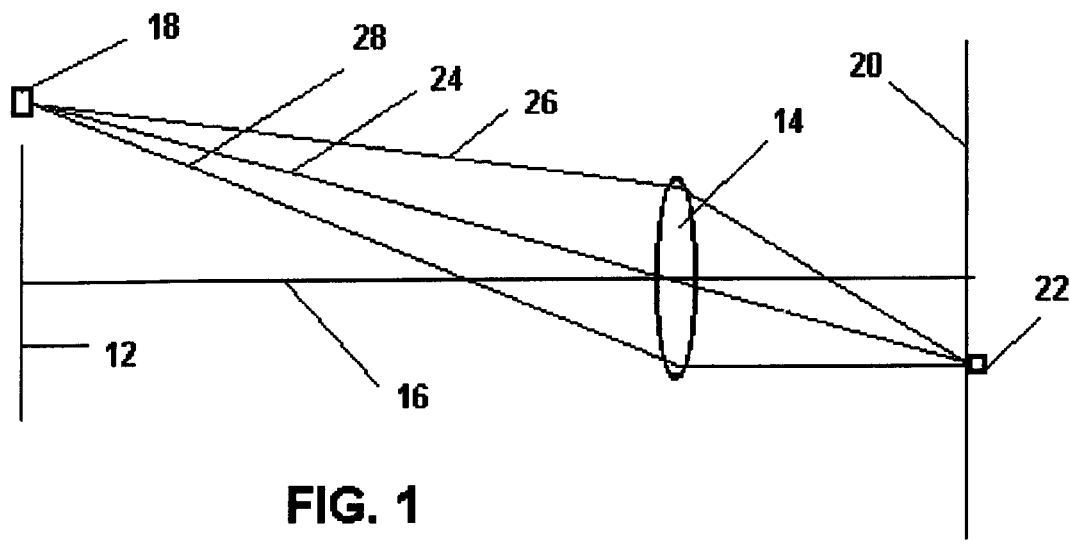
FIG. 1 is a diagram of an imaging system for purposes of defining terminology.
Figure 2:
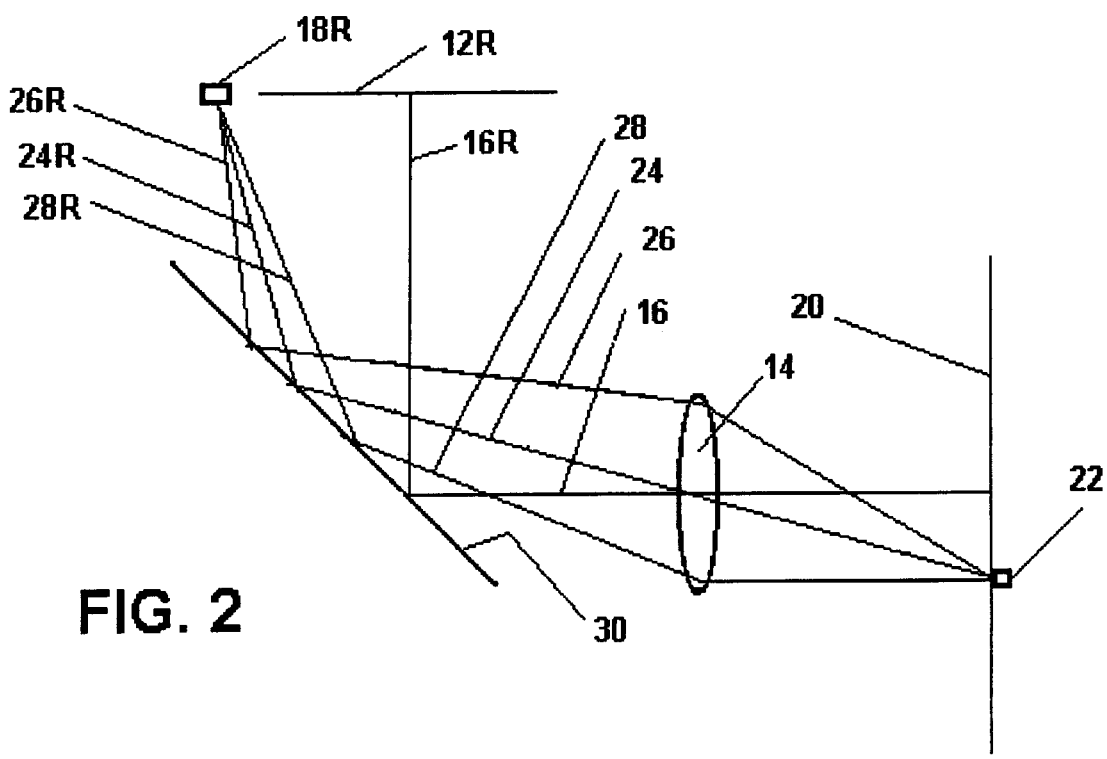
FIG. 2 is a further drawing of an imaging system for purposes of defining terminology.

Referring to FIGS. 1 and 2, there is shown an arrangement for imaging an object 18 in an object plane 12 onto an image plane 20, for purposes of explaining the terminology used in the present application. An imaging system, having a lens 14 with an axis of symmetry 16 for imaging objects 18 in an object plane 12 onto an image plane 20 is conventionally referred to as having an optical axis 16, which frequently is the axis of symmetry of lens 14. Those skilled in the art will recognize that an image of object 18 in object field 12 will be formed as image element 22 in image plane 20. The extent of object field 12 naturally depends upon the size of the image plane 20 and the geometric configuration of the imaging system. In connection with describing the present invention, the optical axis 16 of a camera containing a lens 14 and an image plane 20 is generally referred to as describing the central axis of the imaging system, such as optical axis 16. It will be recognized by those skilled in the art that the actual light path from object 18 to object image 22 follows a direction 24 and includes light at the periphery of lens 14 following optical paths 26 and 28 which are diffracted by lens 14 in connection with forming object image 22. The light paths 24, 26 and 28, while having a direction which is different than that of optical axis 16 are referred to herein as corresponding to the optical access, since the optical axis 16 relates to the center of image plane 20 and objects on one or the other side of optical axis 16 will form images in object plane 20.

FIG. 2 shows a configuration wherein a reflector 30, such as a mirror or an internally reflecting surface of a prism is used in connection with the formation of an image of an object on an object plane 20. Mirror 30 has the effect of reflecting an image on optical axis 16R into optical axis 16. The actual light rays from objects 24R, 26R and 28R are likewise reflected by mirror 30. In connection with describing the present invention, image of object 18R, which follows paths 24R, 26R and 28R via mirror 30 to object image 22 in image plane 20 are said to correspond to optical axis 16R. Mirror 30 reflects, or more generally "deflects" the image from a direction corresponding optical axis 16R to a direction corresponding to axis 16.

Figure 3:
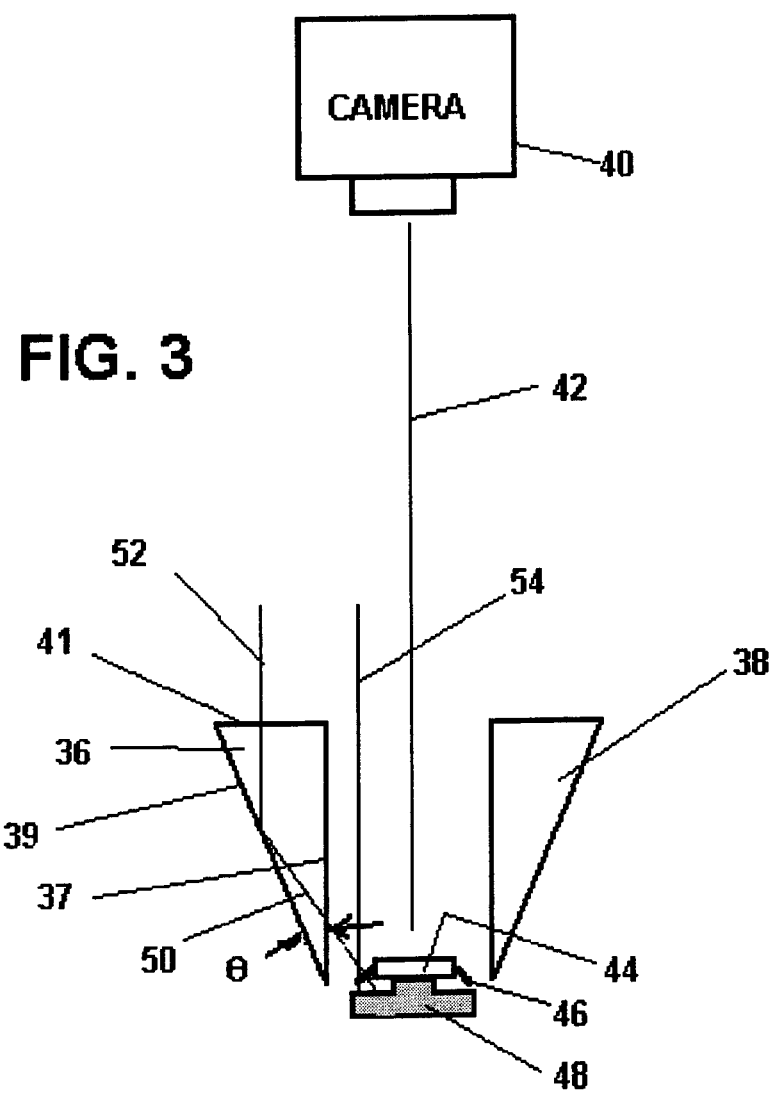
FIG. 3 is a diagram illustrating the arrangement of a first embodiment of the present invention.

FIG. 3 is a diagram illustrating a first embodiment of the present invention for providing images of semiconductor device edges and leads which extends from the edges. A camera, such as a digital CCD camera 40, is arranged with an optical axis 42 facing toward a device-inspection station containing semiconductor device 44. Device 44 in the configuration of FIG. 3 fits on an inspection station platform 48 which provides backlight illumination of the edges and leads 46 of device 44. The diffuse illumination is over a range of directions which include directions corresponding to optical axis 42 and directions corresponding to optical axis 50. Platform 48, may, for example, comprise a transparent plastic platform having etched surfaces which cause diffusion of light. Light may be supplied to platform 48 by use of embedded LED's or by providing other internal illumination which causes the surfaces of platform 48 to provide diffuse backlight illumination for viewing of the edges and leads of semiconductor device 44.

In the embodiment of FIG. 3 a direct view of semiconductor device 44 along direction 54 which corresponds to optical axis 42 is formed as an image in CCD camera 40. The image comprises a backlight top view of device 44 and leads 46 extending on opposite sides of device 44. As may be seen in FIG. 3 the illuminated platform 48 provides a direct backlighting of leads 46 and the edges of the device 44.

In the embodiment of FIG. 3 there are provided first and second prisms 36 and 38 for deflecting a second backlit image of the edges and leads 46 on each side of device 44 and leads 46 for imaging in camera 40. Light emanating from the diffuse illuminator 48 generally along a second optical axis 50 is internally reflected in prism 36 onto a path 52 which corresponds to the first optical access 42, so that a second backlit image of the edges and leads 46 of semiconductor device 44 is formed in the image plane of CCD camera 40. Like the first image, the second image is also a backlit image.

Those skilled in the art will recognize that a prism provides total internal reflection when the angle of incidence of light along optical axis 50 strike reflecting surface 39 at an internal angle of incidence which exceeds the "critical angle" as measured from the internally normal direction of surface 39. This must take into account diffraction which occurs at optical surface 37, through which the image along optical axis 50 passes. The image reflected by optical surface 39 passes through optical surface 41 which is perpendicular to first optical axis 42. In the arrangement of FIG. 3, prisms 36 and 38 are triangular right angle prisms having an angle between surfaces 37 and 39 which is approximately 30 degrees.

Figure 5:
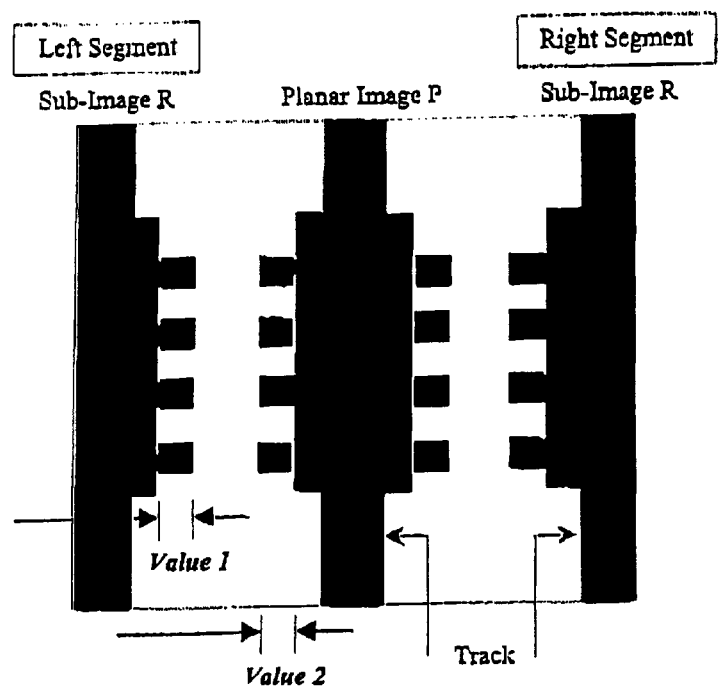
FIG. 5 is a representation of an image formed using the FIG. 3 apparatus.

Referring to FIG. 5 there is shown the image of the semiconductor device 44 and its leads 46 as formed on the image plane of CCD camera 40 using the structure of FIG. 3. A planar image labeled P in FIG. 5 is formed at the center of the image plane of CCD camera 40. Right and left reflected subimages R representing the semiconductor device edges and leads on two opposite sides of the semiconductor device, as reflected internally in prisms 36 and 38 are formed to the sides of the image plane and represent images of the semiconductor devices edges and leads 46 taken along a viewing angle corresponding to optical axis 50.

Those skilled in the art will recognize that from the planar image P of FIG. 5 it is possible to determine the X and Y positions in the plane of the semiconductor device of the leads 46 with respect to the edges of semiconductor body 44. The additional image taken along optical axis 50, shown in FIG. 3, together with the planar image P taken along optical axis 42 enables the determinations not only of the X and Y positions of the leads 46 from edges of the semiconductor device 44 but also a determination of the Z position, which corresponds to the spacing between the lead edges and the semiconductor device body in the vertical direction of FIG. 3.

Figure 6:
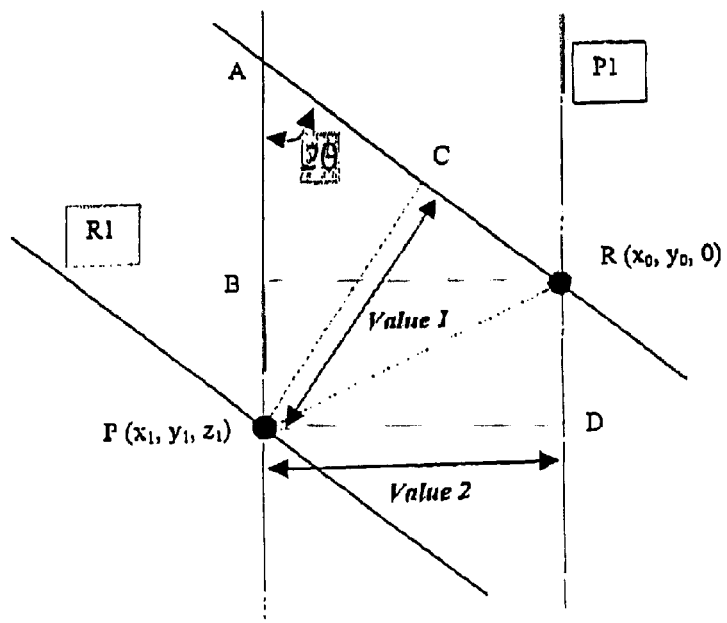
FIG. 6 is a geometrical drawing for purposes of explaining a calculation of lead positions using the FIG. 5 images.

Referring to FIG. 6 there is shown a calculation, by which the Z extension of the lead tips with respect to the device edge can be calculated. It should be recognized that by using planar image P of FIG. 5, the X and Y positions of each of the lead tips can be determined in connection with digitizing the backlit planar image P and analyzing the location of the lead end by methods known in the art.

Referring to FIGS. 5 and 6, value 2 as measured from the captured image in FIG. 5 is the X and Y offset of the lead tip from the device edge represented by position R. Value 1 of FIG. 5 is a corresponding offset of the position of the lead tip from the edge of the device as measured in the image along optical axis 50. The angle between the two images is 2θ, representing the deviation of the direction of optical axis angle 50 from the optical axis 42. The lead standoff, which is the dimension in the Z direction from the device lower edge is given by $$PB = PA - AB = \text{VALUE 1}/\text{SIN } 2\theta - \text{VALUE 2}/\text{TAN } 2\theta.$$

This is shown by the drawing of FIG. 6, which shows the edge location R and lead end location P in the XZ plane for the direct image in direction P1 (corresponding to optical axis 42) and the reflected image in direction R1 (corresponding to optical axis 50).

Figure 4:
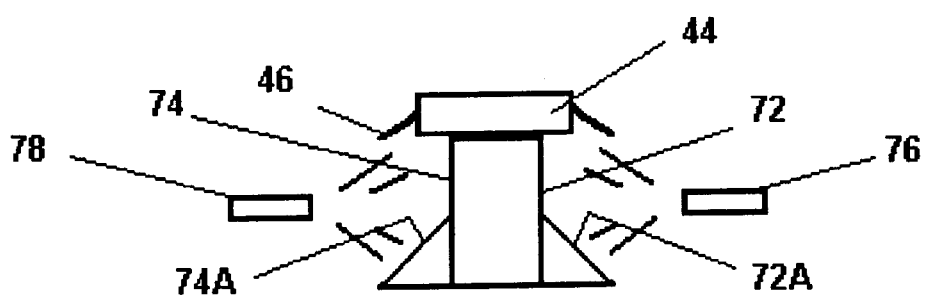
FIG. 4 is a drawing illustrating an alternate embodiment of the inspection station and illuminators for use in the embodiment of FIG. 3.

FIG. 4 is drawing illustrating an alternate arrangement for illuminating the leads 46 and edges of device 44 in connection with the practice of the present invention. In the illustration of FIG. 4 semiconductor device 44 is arranged on a platform 70 which has side surfaces 72 and 74 which are illuminated respectively by diffuse light sources 76 and 78 to provide illumination along optical axis 50. The illumination of surfaces 72 and 74 provide, by reflection, diffusion backlight illumination of the edges of device 44 and projecting leads 46. The platform further includes inclined surfaces 72A and 74A which when illuminated by light sources 76 and 78 provide backlight illumination in directions corresponding to optical axis 42.

Figure 7:
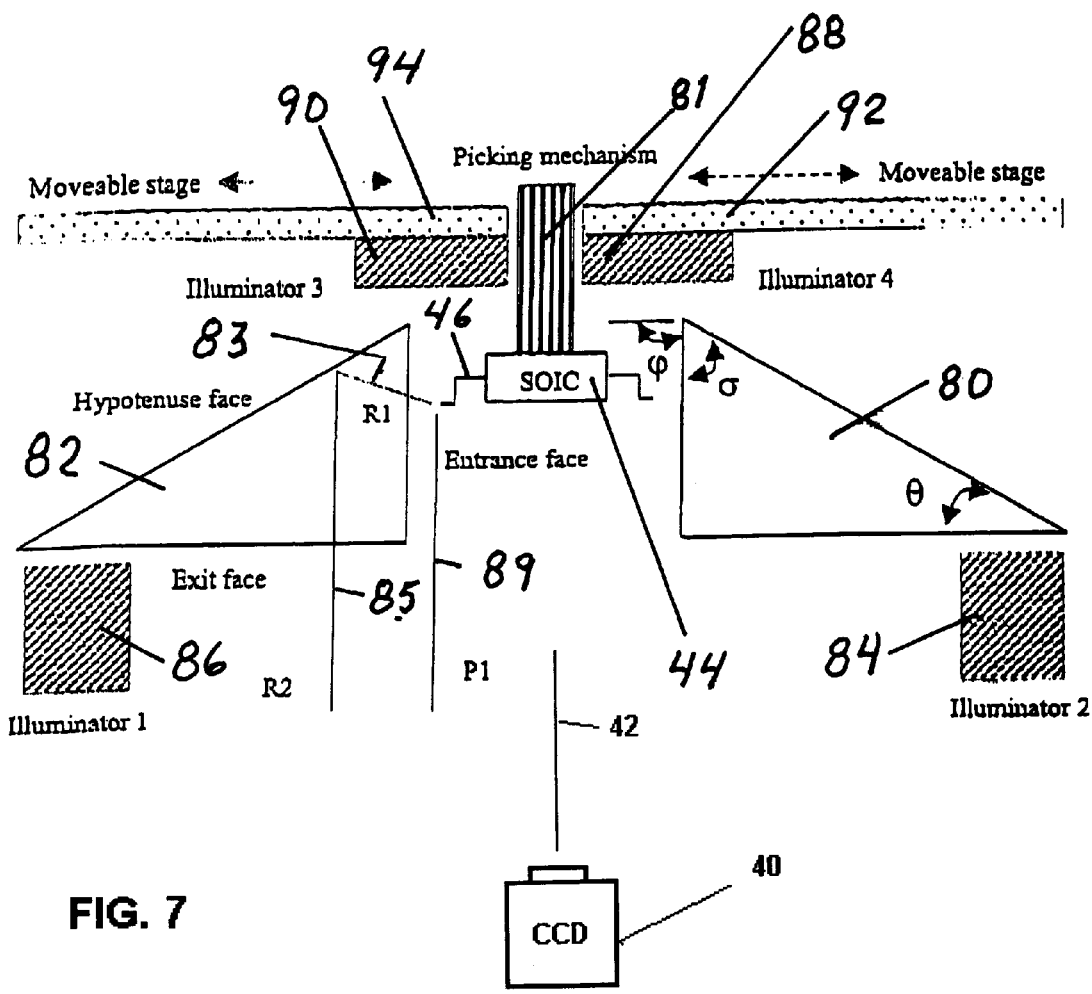
FIG. 7 is a drawing illustrating a second embodiment of the present invention.

FIG. 7 shows a further alternate embodiment of the invention wherein the semiconductor device being inspected is moved to an inspection station by a mechanical picking mechanism. In the configuration of FIG. 7 semiconductor device 44 is held by a mechanical picking mechanism 81 in an inspection station as illustrated. Mechanism 81 is positioned between movable stages 92 and 94 which carry first illumination devices 88 and 90. When semiconductor device 44 is being positioned by mechanism 81, movable stages 92 and 94 are moved away from the inspection station position to allow the semiconductor device to move between illuminated 88 and 90. Thereafter stages 92 and 94 are moved into the inspection positions shown in FIG. 7. Illumination devices 88 and 90 provide diffuse illumination for backlight illumination of the edges of device 44 and leads 46 along optical path 89 which corresponds to optical axis 42 of camera 40. There are provided third and fourth illuminators 84 and 86 which respectively illuminate semiconductor device 44 and leads 46 from the bottom and sides. As shown in FIG. 7 diffuse light from illuminator 84, which may pass through prism 80, provides backlight illumination of device 44 and leads 46 along an optical axis 83 which is reflected in prism 82 to a direction 85 corresponding to optical axis 42. Likewise illumination from illuminator 86 provides backlight illumination of the device edge and leads on the opposite side of device 44 which is interiorly reflected in prism 80 onto a path corresponding to optical axis 42. Accordingly a direct image of device 44 and its leads 46 is provided along a first path corresponding to optical access 42 and along two second optical axes 83 which are reflected within prisms 80, 82 into a direction corresponding optical axis 42.

Figure 8:
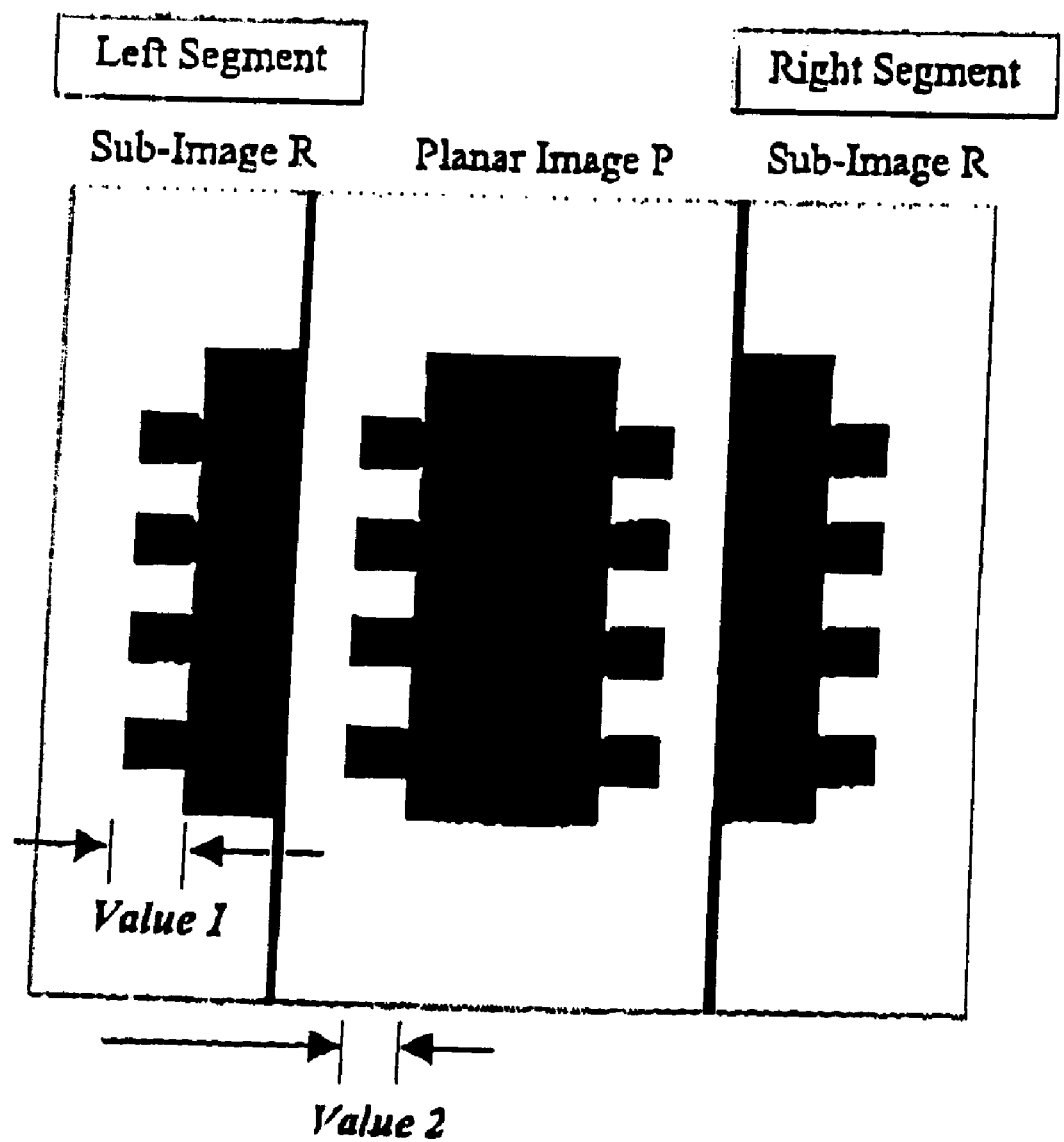
FIG. 8 is a representation of images obtained using the FIG. 7 apparatus.

FIG. 8 is an illustration of the image formed in camera 40 according to the embodiment of FIG. 7. Value 1 and value 2 are derived from the image and lead to similar calculation of the position of leads 46 with respect to the edges of device 44.

Figure 9:
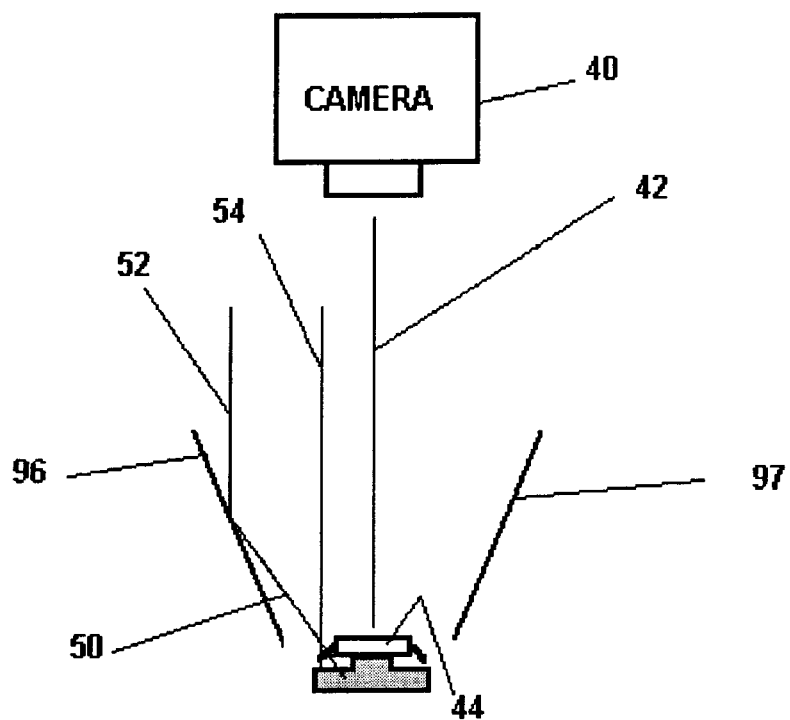
FIG. 9 is a drawing illustrating a third embodiment of the present invention.

Referring to FIG. 9 there is shown a further alternate embodiment of the invention wherein the prisms of the embodiment of FIG. 3 are replaced by mirror surfaces 90, 92 which serve to reflect images along optical access 50 in a direction corresponding to optical access 42. In the example shown the normal direction of mirrors 96, 97 is at an angle of about 60 degrees from first optical axis 42. Those skilled in the art will recognize that the use of mirrors in this configuration is equivalent to the use of prisms.

Figure 10:
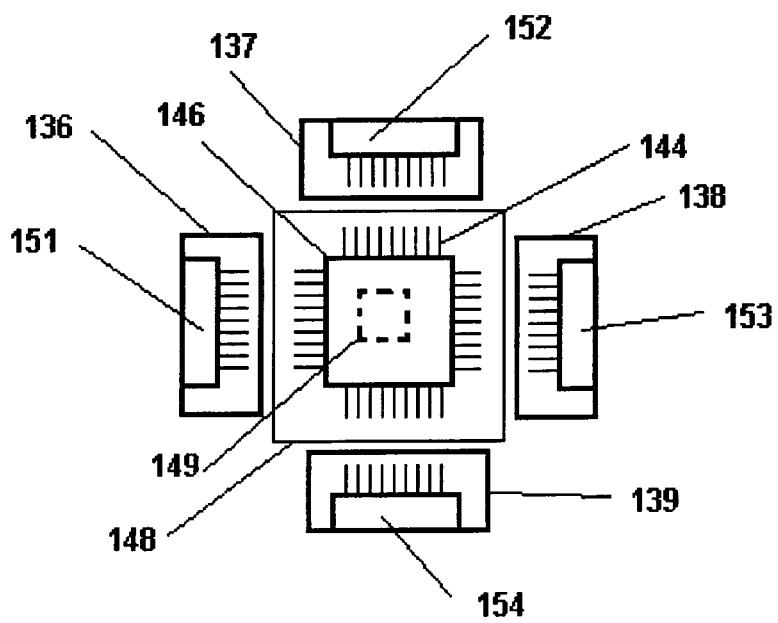
FIG. 10 is a drawing illustrating a fourth embodiment of the present invention.

FIG. 10 shows an inspection station arranged for inspection of leads 144 on four sides of a semiconductor device 146 as viewed on optical axis 42. Device 146 is received on an illuminated platform 148 having a central pedestal 149. Four prims 136, 137, 138 and 139 are arranged on the four sides of platform 148 and reflect backlit images 151, 152, 153 and 154 to direction corresponding to optical axis 42.

While there have been described what are believed to be the preferred embodiments of the invention, those skilled in the art will recognize that other and further changes and modifications may be made thereto without departing from the spirit of the invention, and is intended to claim all such changes and modifications as fall within the true scope of the invention.

I claim:

1. Apparatus for providing first and second backlit images of a semiconductor device edge and lead extending therefrom, said images representative of first and second viewing angles corresponding to first and second different optical axes as measured in a plane perpendicular to said device edge, comprising:

at least one illuminator providing diffuse backlit illumination of said device edge and leads in directions corresponding to said first and second optical axes;

a camera arranged on an opposite side of said device edge from said illuminator along said first optical axis and oriented to form a direct image corresponding to said first optical axis;

a deflector arranged on an opposite side of said device edge and said leads along said second optical axis for deflecting a backlit image of said device edge and leads in a direction corresponding to said second optical axis toward said camera; and a semiconductor device lead inspection system determining a distance L between a lead tip of a lead and the device edge in the direction of the first optical axis, where L is equal to:

$$L = L1/\text{SIN } 2\theta - L2 \text{ TAN } 2\theta$$

and where

L1 is a distance value 1 between the lead tip and the device edge in tile backlit image, L2 is a distance value 2 between the lead tip and the device edge in the direct image, and $2\theta$ is an angle between the first optical axis and the second optical axis.

2. Apparatus as specified in claim 1 wherein aid illuminator comprises an illuminated platform for holding said device.

3. Apparatus as specified in claim 2 wherein said camera is arranged on a side of said device opposite said illuminated platform when said device is received on said platform.

4. Apparatus as specified in claim 3 for providing backlit images of device edges and leads on two opposite sides of the semiconductor device, and including two said deflectors for deflecting images corresponding to two said second optical axes.

5. Apparatus as specified in claim 3 for providing backlit images of device edges and leads on four sides of the semiconductor device, and including four said deflectors for deflecting images corresponding to four said second optical axes.

6. Apparatus as specified in claim 1 wherein said deflector comprises a prism.

7. Apparatus as specified in claim 6 wherein said prism is a right angle prism.

8. Apparatus as specified in claim 7 wherein said prism has a surface parallel to said first optical axis and a surface substantially perpendicular to said first optical axis.

9. Apparatus as specified in claim 1 wherein said deflector comprises a mirror.

10. Apparatus as specified in claim 1 wherein there are provided at least two illuminators, one for back illuminating said device edge and leads in directions corresponding to each of said optical axes.

11. Apparatus as specified in claim 10 wherein at least one of said illuminators is arranged to move between an illuminating position and a with withdrawn position, said withdrawn position facilitating movement of the semiconductor device into a inspection station.

12. A method for providing first and second backlit images of a semiconductor device edge and leads extending therefrom, said images representing first and second viewing angles corresponding to first and second different optical axes as measured in a plane perpendicular to said device edge, for determining a distance between a lead tip and the device edge, comprising:

illuminating said device edge and leads with backlit diffuse illumination radiating in the directions corresponding to said first and second optical axes;

capturing a first backlit direct image of said device edge and said leads in a direction corresponding to said, first optical axis;

deflecting a second backlit image of said device edge and leads from a direction corresponding to said second optical axis into a direction corresponding to said first optical axis;

capturing said second deflected backlit image of said device edge and said leads; and determining a distance L between a lead tip of a lead and the device edge in the direction of the first optical axis, where L is equal to:

$$L = L1/\text{SIN } 2\theta - L2 \text{ TAN } 2\theta$$

and where

L1 is a distance value 1 between the lead tip and the device edge in the second backlit image, L2 is a distance value 2 between the lead tip and the device edge in the first backlit image, and 2θ is an angle between the first optical axis and the second optical axis.

13. A method as specified in claim 12 wherein said illuminating comprises illuminating from at least one illuminator arranged to radiate in reactions corresponding to said first and second optical axis toward said device edge and said leads.

14. A method as specified in claim 13 for providing backlit images of device edges and leads on four sides of the semiconductor device, wherein the first backlit direct image of said four edges and leads is captured in a direction corresponding to said first optical axis and wherein the second backlit image of each of said device edges and leads is deflected from directions corresponding to four of said second optical axis in directions corresponding to said first optical axis, and wherein four of said second deflected backlit images are captured.

15. A method as specified in claim 12 wherein said capturing said first backlit direct image and said second backlit image comprises capturing said images on a single image plane of a camera on a side of said device opposite said at least one illuminator.

16. A method as specified in claim 12 for providing backlit images of device edges and leads on two opposite sides of the semiconductor device, wherein the first backlit direct image of said two edges and leads is captured in a direction corresponding to said first optical axis and wherein the second backlit image of each of said device edges and leads is deflected from directions corresponding to two of said second optical axis in directions corresponding to said first optical axis, and wherein two of said second deflected backlit images are captured.

17. A method as specified in claim 12 wherein said deflecting comprises deflecting by a prism.

18. A method as specified in claim 17 wherein said deflecting includes internal reflection in said prism.

19. A method as specified in claim 12 wherein said deflection comprises reflection by a mirror.

20. A method as specified in claim 12 wherein said illumination comprises illuminating said device edge and leads from a first illuminator in directions corresponding to said first optical axis and illuminating said device edge and lead from a second illuminator in directions corresponding to said second optical axis.

21. A method according to claim 20 further comprising moving said first illuminator between a first position for illuminating said device edge and said leads and a second withdrawn position facilitating movement of the semiconductor device into an inspection position.

22. The method of claim 12 further comprising determining the location of one or more lead tips using the first backlit direct image and the second backlit image.

* * * * *

UNITED STATES PATENT AND TRADEMARK OFFICE
CERTIFICATE OF CORRECTION

PATENT NO.  : 6,567,161 B1
DATED       : May 20, 2003
INVENTOR(S) : Pao Meng Lee It is certified that error appears in the above-identified patent and that said Letters Patent is hereby corrected as shown below:

Column 6,
Line 14, replace "lead", with -- leads --.
Line 40, replace "tile", with -- the --.
Line 45, replace "aid", with -- said --.

Column 7,
Line 47, replace "reactions", with -- directions --.

Signed and Sealed this

Twenty-third Day of September, 2003

JAMES E. ROGAN
*Director of the United States Patent and Trademark Office*